(12) United States Patent
Buermann

(10) Patent No.: US 6,765,676 B1
(45) Date of Patent: Jul. 20, 2004

(54) SIMULTANEOUS COMPENSATION OF SOURCE AND DETECTOR DRIFT IN OPTICAL SYSTEMS

(75) Inventor: Dale Buermann, Los Altos, CA (US)

(73) Assignee: N & K Technology, Inc., Santa Clara, CA (US)

( * ) Notice: Subject to any disclaimer, the term of this patent is extended or adjusted under 35 U.S.C. 154(b) by 193 days.

(21) Appl. No.: 09/651,421

(22) Filed: Aug. 30, 2000

(51) Int. Cl.[7] .............................................. G01N 21/55
(52) U.S. Cl. ...................................................... 356/448
(58) Field of Search ................................ 356/433, 434, 356/435, 445, 447, 448

(56) References Cited

U.S. PATENT DOCUMENTS

| | | | |
|---|---|---|---|
| 4,830,504 A | * | 5/1989 | Frohardt et al. ............ 358/448 |
| 4,905,170 A | | 2/1990 | Forouhi et al. ............ 364/556 |
| 5,028,800 A | * | 7/1991 | Wulf et al. ................ 250/575 |
| 5,054,878 A | | 10/1991 | Gergely et al. .............. 385/33 |
| 5,315,111 A | | 5/1994 | Burns et al. ................ 250/235 |
| 5,910,842 A | * | 6/1999 | Piwonka-Corle et al. ... 356/369 |

* cited by examiner

Primary Examiner—Richard A. Rosenberger
(74) Attorney, Agent, or Firm—Lumen Intellectual Property Services, Inc.

(57) ABSTRACT

An optical system for simultaneously compensating a source drift of a light source and a detector drift of a light detector includes a test location, a first beam path from the light source to the test location, a second beam path from the test location to the light detector. First and second beam paths are arranged to intersect at a beam crossing. A calibration sample having a known reflectivity is positioned at the test location and illuminated by a probe beam generated by the light source. A known response beam of the calibration sample is used for calibrating the light source and the detector. A reference sample is placed at the beam crossing and illuminated by the probe beam. In response, the reference sample sends a reference beam along the second path length, which is used for compensating the source and detector drift.

25 Claims, 5 Drawing Sheets

SIMULTANEOUS COMPENSATION OF SOURCE AND DETECTOR DRIFT IN OPTICAL SYSTEMS

FIELD OF THE INVENTION

This invention relates to optical systems for performing measurements, and in particular to an apparatus and method for simultaneous compensation of drift occurring in a light source and in a light detector.

BACKGROUND AND PRIOR ART

In many fields optical measurement methods are preferred over other approaches because of their non-destructive nature and high accuracy. For example, measurements of reflected or transmitted light can be used to determine numerous physical properties of objects. In fact, optical measurements can be used to study the surface and the interior of objects or of the layers of which the objects are made. The basic physical parameters which can be derived from the study of reflected and transmitted light include thickness, index of refraction, extinction coefficient, surface roughness and energy bandgap of the material making up the object or of a particular layer of the object, e.g., the top layer. Other properties and information about the object and/or its layers, such as material composition, mechanical condition, doping level etc. can be derived from these basic physical parameters.

The prior art teaches optical systems for performing optical measurements using light reflected and/or transmitted by the object being studied. Furthermore, methods for analyzing the reflectance and transmittance data, e.g., spectrum, polarization, intensity and other characteristics of the reflected or transmitted light are also known. For example, in U.S. Pat. No. 4,905,170 Forouhi et al. describe an optical method for determining physical parameters of thin films based on reflectivity or transmittance data obtained over a range of wavelengths.

Further improvements in optical measurement and analysis techniques are frequently hampered by hardware problems. Specifically, light sources delivering the light incident on the samples are subject to intensity fluctuations. Also, light detectors positioned to receive the reflected or transmitted light are subject to fluctuations in detection sensitivity. These fluctuations are typically non-uniform across any given wavelength range and difficult to predict or unpredictable. They are caused by external influences such as temperature, pressure, humidity and operating conditions such as mechanical vibration, current, wear, aging and others.

Over time, source and detector fluctuations add up to produce source and detector drift. In general, the drift in the light source is not related to the drift in the light detector. Thus, in some cases the relative drift between source and detector can be the sum of the drifts.

FIG. 1 shows a simplified prior art optical measurement system 10 having a light source 16 for illuminating a test sample 12 with a probe beam 18, and a detector 20 for receiving a reflected beam 22. Source 16 spans a certain wavelength range. The intensity $I_s$ of beam 18 is graphed adjacent source 16 as a function of wavelength $\lambda$ at an initial time $t_0$, e.g., at start-up, and at a later time $t_1$, e.g., after several minutes of operation. Likewise, the detection signal $I_d$ of detector 20 is graphed adjacent detector 20 at times $t_0$ and $t_1$. At time $t_1$ the source drift and detector drift are clearly significant and not correlated over the wavelength range. Hence, any calibration between source intensity $I_s$ and detector signal $I_d$ at time $t_0$ can not be used for compensating the source and detector drifts at time $t_1$.

The prior art teaches to compensate for source drift in optical systems. For example, U.S. Pat. No. 5,054,878 to John S. Gergely et al. teaches a device that automatically compensates for source light drift at the output end. In this invention, the output of the light source is coupled into a fiber optic, and a portion of the light output from the fiber optic is directed into a calibrated photodiode. The calibrated photodiode is connected to a transimpedance amplifier. The remainder of the light output by the fiber optic is focused into a test sample, and the light reflected from the test sample is measured using a detector. The signal detected at the detector is compared with the signal read at the transimpedance amplifier. To compensate for the drift in the light source, the signal from the transimpedance amplifier is divided into the signal from the detector.

The solution of Gergely et al. does not account for detector drift. In fact, most prior art solutions concentrate on stabilizing or compensating the light source by adjusting the external parameters and/or the operating conditions. For example, source intensity is often compensated by adjusting the power supply (operating current) or varying the operating temperature (active heating and/or cooling). Meanwhile, detector drift is either assumed to be negligible and not taken into account or re-calibrated on an infrequent basis.

Advanced prior art optical measurement techniques, e.g., the Forouhi and Bloomer method, are very sensitive to drift. Hence, independent and uncorrelated drift in source and detector will prevent such techniques from yielding accurate values of physical parameters of test samples.

In addition, in some testing environments the optical measurement can not be interrupted to re-calibrate the source and/or the detector. This may be the case when the test sample is located in a controlled environment, e.g., a vacuum chamber, or when the measurement cycle is long and can not be halted. Under these conditions the optical measurement becomes progressively less accurate.

It would be an advance in the art to provide for simultaneous source and detector drift compensation without requiring that the measurement be stopped and without having to access the test sample.

OBJECTS AND ADVANTAGES

In view of the above, it is the object of the present invention to provide an apparatus and method for simultaneous source and detector drift compensation in optical systems. In fact, the object of the invention is to compensate for drifts occurring in the source and detector over time with minimal disruption to the optical system and without disturbing the test sample.

It is another object of the invention to provide an apparatus for source and detector drift compensation which can be used at any time during a measurement cycle in an optical measurement system.

Yet another object of the invention is to provide a simple and inexpensive apparatus for drift compensation which is easy to use.

Further objects and advantages of the invention will become apparent upon reviewing the below specification.

SUMMARY OF THE INVENTION

The objects and advantages of the invention are attained by a method for simultaneously compensating a source drift of a light source and a detector drift of a light detector. A first beam path is provided for a probe beam generated by the source and traveling from the light source to a test location. A second beam path is provided from the test location to the light detector. The beam paths are arranged to intersect or cross at a beam crossing.

A calibration sample is positioned at the test location and illuminated by the probe beam. In response, the calibration sample sends a known response beam along the second beam path to the light detector. The light source and the light detector are calibrated using this known response beam from the calibration sample. For compensation, a reference sample is placed at the beam crossing. The reference sample is positioned such that in response to illumination by the probe beam it sends a reference beam along the second beam path to the light detector. This reference beam is used to simultaneously compensate the source and detector drift. Conveniently, the calibration sample is a highly reflective sample of well-known reflectivity.

The compensation step can be repeated at any time by inserting the reference sample at the beam crossing after calibration of the light source and detector. The compensation is based on a relation established between the known response beam and reference beam. For example, the relation can be established based on the detector current intensities obtained while receiving the known response beam and the reference beam.

During testing a test sample is placed at the test location and illuminated by the probe beam. In response, the test sample sends a response beam along the second beam path to the light detector. In accordance with the invention, compensation of source and detector drift can be performed while the test sample is in place at the test location by inserting the reference sample at the beam crossing.

It is convenient when the reference sample is selected to have a particular response level to the probe beam. In particular, the intensity of the reference beam generated by the sample is preferably within a certain range of the intensity of the response beam from the test sample. It is also convenient when the probe and response beams are collimated at the beam crossing.

A system for simultaneously compensating source and detector drift in accordance with the invention includes the test location, the first beam path and the second beam path intersecting the first beam path at the beam crossing. Furthermore, the system has the calibration sample producing a known response beam to the probe beam and the reference sample for placing at the beam crossing. A first control unit, which controls the sensitivity of the detector, is used for calibrating the light source and detector using the response beam. A second control unit, which controls the intensity of the light source, is then employed for compensating the source and detector drift using the reference beam. In fact, the first and second control units can be integrated in one control unit.

The light source can be any suitable light source spanning the desired wavelength range and can include incandescent bulbs, lasers and gas discharge tubes or any combination of such sources. For example, in measurements requiring reflectance or transmittance data in various portions of the spectrum, the source can be a broadband source made up of a laser and a discharge tube. Correspondingly, a broadband detector or a photospectrometer is chosen as the light detector.

Any known optical elements such as lenses, mirrors, gratings and other beam guiding elements can be used to guide probe and response beams between the source, test location and detector along their optical paths. When using broadband sources and detectors the use of reflective optics such as mirrors in the beam paths of probe and response beams in preferred to refractive optics. In one embodiment, the first beam path has a first mirror, such as a first toroidal mirror for guiding the probe beam. In fact, the first toroidal mirror collimates the probe beam to produce a collimated probe beam. A second toroidal mirror can be positioned to focus the collimated probe beam, e.g., into a fiber for delivery to the calibration sample or directly into the calibration sample. In another embodiment or in the same embodiment the response beam is collimated by a third toroidal mirror to produce a collimated response beam. The collimated response beam is then focused by a fourth toroidal mirrors on the detector. It is preferable that the beam crossing be between collimated probe and collimated response beams. It is further preferred that a first optical path length from the first toroidal mirror to the second toroidal mirror and a second path length from the first toroidal mirror to the fourth toroidal mirror be equal.

DETAILED DESCRIPTION

Figure 1:
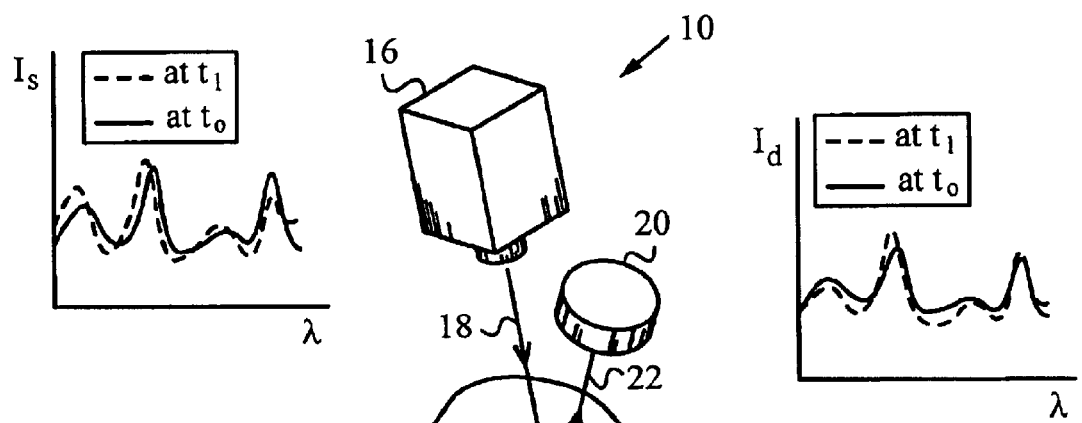
FIG. 1 is a simplified prior art optical measurement arrangement exhibiting source and detector drift.
Figure 2:
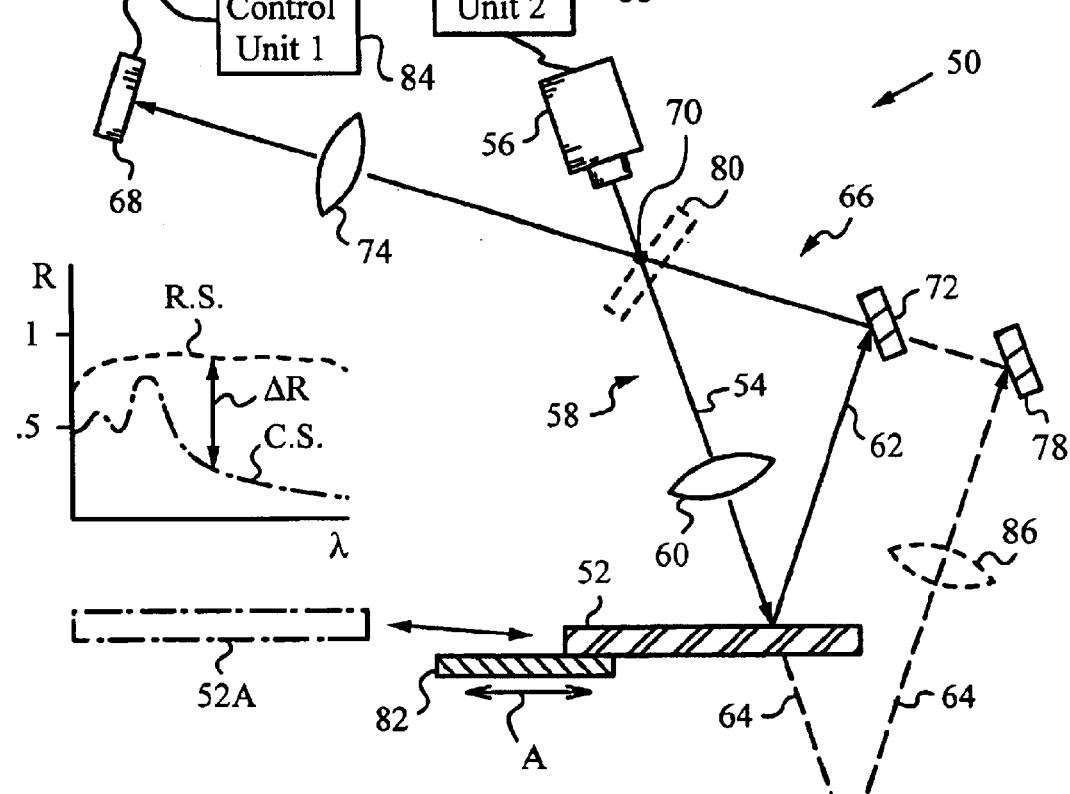
FIG. 2 is a schematic view of an optical system according to the invention.

FIG. 2 illustrates an optical system 50 for simultaneously compensating a source drift and a detector drift, which is used to measure physical properties of a test sample. As shown in FIG. 2, a calibration sample 52 is positioned at a test location and illuminated with a probe beam 54. Probe beam 54 is generated by a light source 56. Light source 56 can be a laser, a incandescent bulb, a gas discharge tube or any other light source capable of generating probe beam 54 of requisite characteristics. In many applications, probe beam 54 has to span a particular wavelength range $\Delta\lambda$. When wavelength range $\Delta\lambda$ is large, several light sources may be combined to form a broadband source.

Probe beam 54 propagates from light source 56 to calibration sample 52 along a first optical beam path 58. Any number of optical elements such as lenses, mirrors, gratings and other beam guiding elements can be used in beam path 58 to guide probe beam 54 to calibration sample 52. In the present embodiment a focussing lens 60 is positioned in beam path 58 to focus probe beam 54 on calibration sample 52.

Upon illumination with probe beam 54 calibration sample 52 generates a known response beam, which is used for calibrating the light source 56 and the detector 68. Depending on calibration sample 52 and probe beam 54, the known response beam can be a reflected beam 62, a transmitted beam 64 or both. Thus, either or both beams 62, 64 can be treated as the response beam. Calibration sample 52 typically is a silicon sample whose reflection characteristics are well-known (e.g., can get from literature or measurement on another device). In the present discussion we will first treat only reflected beam 62 as the response beam.

Reflected beam 62 propagates along a second optical beam path 66 from calibration sample 52 to a light detector 68. Light detector 68 can be any suitable light sensitive device such as a photodetector, a charge coupled device, a phototransistor, a spectrophotometer or any other photosensitive device. When source 56 is a broadband source then detector 68 is preferably a broadband detector, e.g., a spectrophotometer, sensitive to light spanning the entire wavelength range $\Delta\lambda$.

Second beam path 66 is arranged such that it crosses first beam path 58 at a beam crossing 70. In other words, probe beam 54 and response beam, in this case reflected beam 62, are guided such that they cross at beam crossing 70. This can be accomplished by using any suitable beam guiding elements in beam paths 58, 66. In this embodiment a mirror 72 is used in second beam path 66 to re-direct reflected beam 62 such that it crosses probe beam 54 at beam crossing 70. Also, a focussing lens 74 is also positioned in second beam path 66 for focussing reflected beam 62 on detector 68. It will be clear to a person skilled in the art that optical elements used in beam paths 58, 66 to produce beam crossing 70 and properly guide probe and response beams 54, 62 will depend on the geometry of optical system 50.

When transmitted beam 64 is used as the response beam two planar mirrors 76, 78 guide transmitted beam 64 to cross probe beam 54 at beam crossing 70. Also, a focusing lens 86 is positioned between two planar mirrors 76, 78 for preventing the divergence of the transmitted beam 64. Again, a person skilled in the art will recognize that the optical elements to cross transmitted beam 64 with probe beam 54 at beam crossing 70 will depend on the geometry of optical system 50.

A removable reference sample 80 indicated in a dashed line is positioned at beam crossing 70. Preferably, a mechanical or an electromechanical unit (not shown) is used to place reference sample 80 at beam crossing 70 and remove it during measurement of a test sample. Reference sample 80 is a reflective sample over an entire wavelength range $\Delta\lambda$ of probe beam 54, and when in place at beam crossing 70 it reflects probe beam 54 to detector 68. The reflectivity R of the reference sample 80 is high enough to get a signal. For example, when probe beam 54 spans a wavelength range from 120 nm to 2000 nm reference sample 80 is a quartz sample exhibiting a nearly uniform 100% reflectivity over this wavelength range. Furthermore, the reflectivity of reference sample 80 can be closed to that of remainder of optical system 50 for dynamic range purpose within a predetermined range.

Calibration sample 52 positioned at the test location is held on a stage 82, of which only a portion is shown. Stage 82 enables calibration sample 52 to be moved or scanned as indicated by arrow A. In fact, stage 82 can be of the type permitting displacement of calibration sample 52 in any desired direction. In some embodiments calibration sample 52 is kept in a controlled environment, e.g., in a vacuum chamber. In these cases stage 82 will exhibit the necessary adaptations, as is known in the art.

First control units 84 is connected to detector 68 for controlling the detection sensitivity over wavelength range $\Delta\lambda$. Second control unit 88 is connected to light source 56 for controlling the light intensity over wavelength range $\Delta\lambda$. In particular, control units 84 and 88 have suitable amplification stages (not shown) to perform these adjustments. Alternatively, control units 84 and 88 can be connected to control mechanisms of source 56 and detector 68 respectively. In yet another embodiment, additional tuning and/or adjustment devices can be used to control the intensity of light source 56 and sensitivity of detector 68. In fact, any approaches to controlling source intensity and detection sensitivity known in the art can be employed. Alternatively, first and second control units 84 and 88 can be integrated in one control unit 90.

To calibrate the light source 56 and the detector 68, optical system 50 is first operated with the reference sample 80 removed from beam crossing 70. Calibration sample 52 is a reflective sample over wavelength range $\Delta\lambda$ and has a known reflectivity R, such as silicon wafer. For example, the reflectivity R of silicon sample 52 is about 50% from 120 nm to 2000 nm (refer to a graph of reflectivity as a function of wavelength $\lambda$ in FIG. 2).

In the present embodiment light source 56 delivers probe beam 54 covering wavelength range $\Delta\lambda$ and calibration sample 52 has a reflectivity R of approximately 100% across that wavelength range. In most cases, however, reflectivity R will vary as a function of wavelength $\lambda$; $R=R(\lambda)$. The intensity $I_s$ of probe beam 54 is variable over wavelength range $\Delta\lambda$. In other words, $I_s$ of probe beam 54 is also a function of wavelength $\lambda$; $I_s=I_s(\lambda)$. Detector 68 is sensitive to light spanning wavelength range $\Delta\lambda$. However, the response of detector 68 is assumed to be linear since the response may differ with $\lambda$, but current to number of photon is linear.

When probe beam 54 is turned on it propagates along first beam path 58 and is incident on calibration sample 52. In response, calibration sample 52 sends a known response beam in reflected beams 62 along the second beam path 66 to the light detector 68. Since the reflectivity of calibration sample 52 is R, the following relationship exists between intensity $I_s$ and detection signal $I_d$:

$$I_d = [R+\gamma(\lambda)]I_s,$$

where $\gamma(\lambda)$ is conditioned by system 50 and in particular the optical components in first and second beam paths 58 and 66. The entire spectrum of light of the known response beam is used for calibrating the light source 56 and the detector 68.

Control unit 84 now performs a relative calibration of source 56 and detector 68 by adjusting the sensitivity of the detector 68. Adjusting the intensity of detector 68 is preferable because turning up the light source 56 will alter a gain across the spectrum at different rates. However, if the light source 56 is a narrow band source, e.g., single $\lambda$ value, adjusting the intensity of the light source 56 is also preferable. Also, either of the detector 68 and the light source 56 should not be adjusted after baseline is set. Furthermore, control unit 84 is not necessary for some applications. The relative calibration of source 56 and detector 68 is performed by adding a "$\delta R$" value to the data to maintain the $\Delta R$ value between the known response beam and reference beam, which is shown in the graph with respect to FIG. 2

Thus, relative calibration establishes a linear relationship between intensity value $I_s$ and corresponding detection signal $I_d$ across entire wavelength range $\Delta\lambda$.

During regular operation a test sample 52A (shown in dashed line) is positioned in the place of calibration sample 52, e.g., at the test location on stage 82, and the response beam, i.e., either reflected beam 62 or transmitted beam 64

(or both), is detected by detector 68. The data obtained from the response beam is used to analyze the physical properties of test sample 52 in accordance with any suitable technique known in the art. Furthermore, this method can be used to study the reflectivity characteristics of all the optical components in optical system 50 by operating this optical system without a test sample in place and with a 100% reflectivity test sample in place.

After a set time period or whenever drift of source 56 and/or detector 68 affects the measurement process, reference sample 80 is placed at beam crossing 70 while the test sample 52 is in place at the test location. As a result, probe beam 54 is reflected directly to detector 68 through lens 74. The reference sample 80 sends a reference beam along the second beam path 66 to the light detector 68 in response to illumination by the probe beam 54. This reference beam is used to simultaneously compensate the source and the detector drift of the optical system 50. The compensation step can be repeated at any time by inserting the reference sample 80 at the beam crossing 70 after calibration of the light source 56 and detector 68 using calibration sample 52. The compensation is based on a relation established between the known response of calibration sample 52 and reference beam of reference sample 80. For example, the relation can be established based on the detector current intensities obtained while receiving the known response beam and the reference beam.

Now a simultaneous compensation of source 56 and detector 68 drifts is performed by control unit 88 to re-establish the relative calibration. Intensity $I_s$ of source 56 can be adjusted to re-establish relative calibration. It should be noted that this re-calibration or re-establishment of relative calibration accounts simultaneously for both source and detector drifts, although no absolute calibration is achieved.

Figure 3:
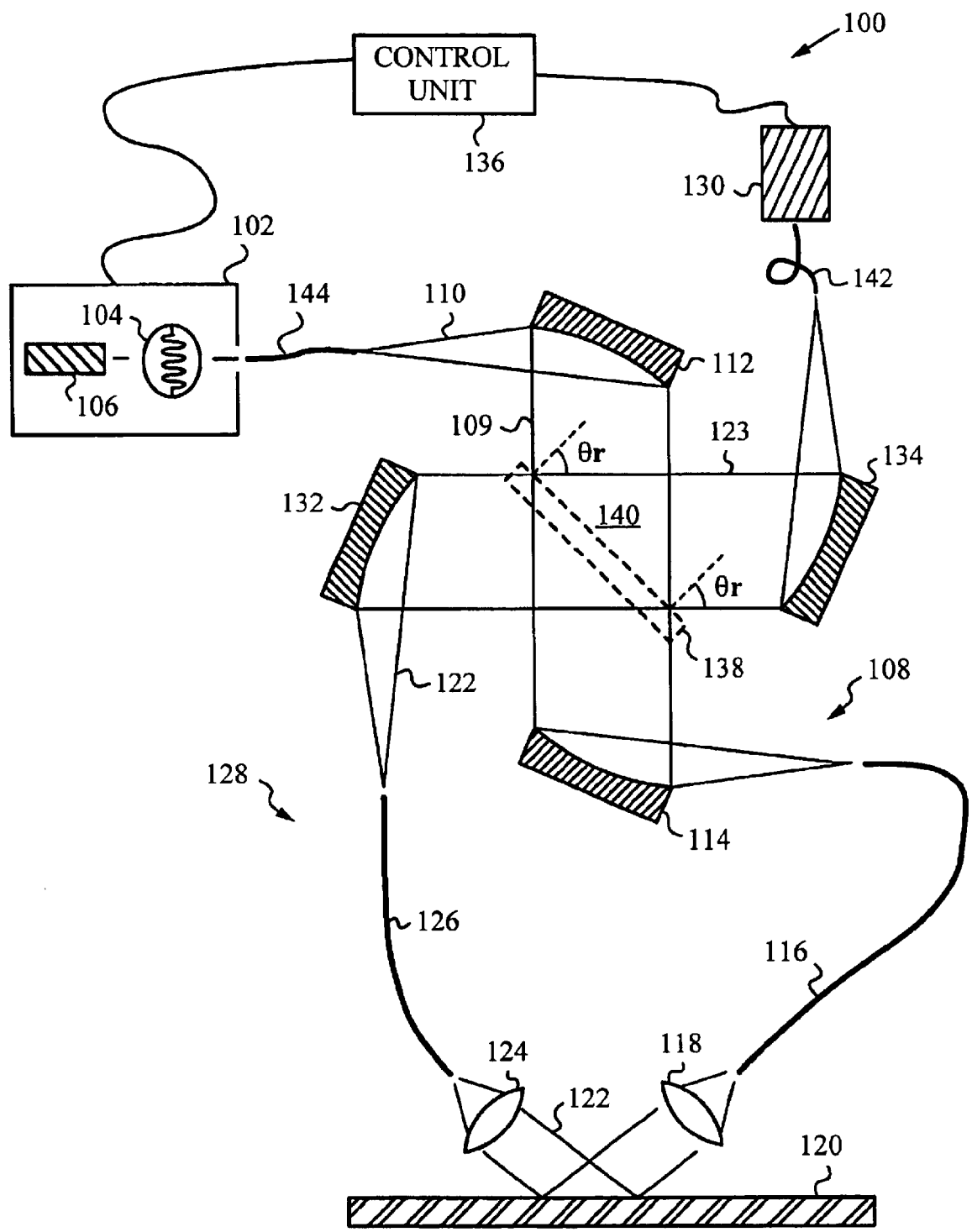
FIG. 3 is a schematic view of an embodiment of an optical system according to the invention using reflective optics.

A preferred embodiment of an optical system 100 according to the invention is illustrated in FIG. 3. In this embodiment a light source 102 is an integrated source having a gas discharge tube 104 and a laser 106 for spanning a wide wavelength range $\Delta\lambda$.

A first beam path 108 for a probe beam 110 emitted from source 102 and coupled to an optical fiber 144 has a first toroidal mirror 112 and a second toroidal mirror 114. First toroidal mirror 112 collimates probe beam 108 to produce a collimated probe beam 109. Second toroidal mirror 114 focuses collimated probe beam 109 into an optical fiber 116.

Optical fiber 116 guides probe beam 110 to a focussing lens 118 which focuses probe beam 110 on a calibration sample 120. Calibration sample 120 reflects a portion of the incident light from probe beam 110 in the form of reflected beam 122, which is the response beam in this embodiment.

Response beam 122 is guided along a second beam path 128 from calibration sample 120 to a light detector 130. In particular, response beam 122 is focussed by a focussing lens 124 into an optical fiber 126. Optical fiber 126 guides response beam 122 to a third toroidal mirror 132 which collimates response beam 122. Thus, a collimated response beam 123 is reflected from third toroidal mirror 132 to a fourth toroidal mirror 134. Fourth toroidal mirror 134 focuses response beam 122 into an optical fiber 142 on detector 130.

An integrated control unit 136 connected to detector 130 and to light source 102 controls these to obtain relative calibration and to re-establish the relative calibration during regular operation of testing a test sample in the manner discussed above. To re-establish relative calibration during operation, a reference sample 138 is placed at a beam crossing 140 between probe beam 110 and response beam 122. In fact, beam crossing 140 is actually between collimated probe beam 109 and collimated response beam 122. This location of beam crossing 140 is advantageous because angle $\theta_r$ is nearly the same for the whole beam whereas a non-collimated beam has different $\theta_r$ (as shown in FIG. 6). In addition, this location of beam crossing 140 is better for imaging point to point, e.g., for imaging source 102 into fiber 116 and fiber 126 into detector 130.

The use of optical fibers 116 and 126 in guiding probe beam 110 and response beam 122 is advantageous due to the mechanical flexibility optical fibers. This flexibility permits the user to alter the arrangement of optical system 100 with minimal effort and in short time.

Figure 4:
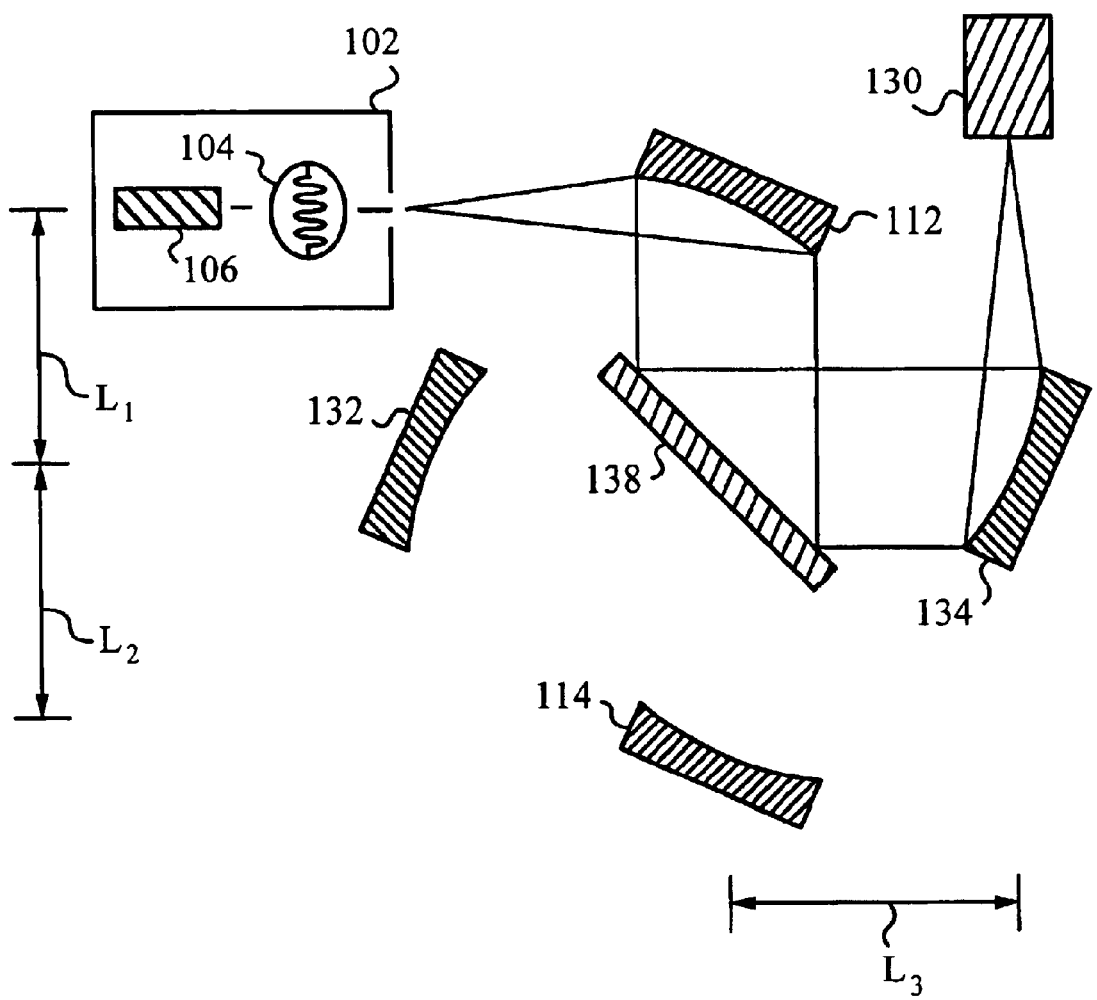
FIG. 4 is a schematic view illustrating a portion of the optical system of FIG. 3.

A further advantageous aspect optical system 100 is illustrated in the partial view of FIG. 4. Here the re-establishment of relative calibration between source 102 and detector 130 is being effectuated while reference sample 138 is in place at beam crossing 140. The optical path length between first toroidal mirror 112 and second toroidal mirror 114 is equal to $L_1+L_3$. The optical path length from first toroidal mirror 112 to second toroidal mirror 114 is equal to $L_1+L_2$. It is preferable that $L_2=L_3$ such that the optical path lengths from first to second toroidal mirrors and from first to fourth toroidal mirrors are equal. In this manner any effects of system 100 on the propagation of probe beam 110 are factored out.

A further advantage optical system 100 resides in its usage of toroidal mirrors. This is especially important when $\Delta\lambda$ is very large since chromatic effects are thus minimized.

Figure 5:
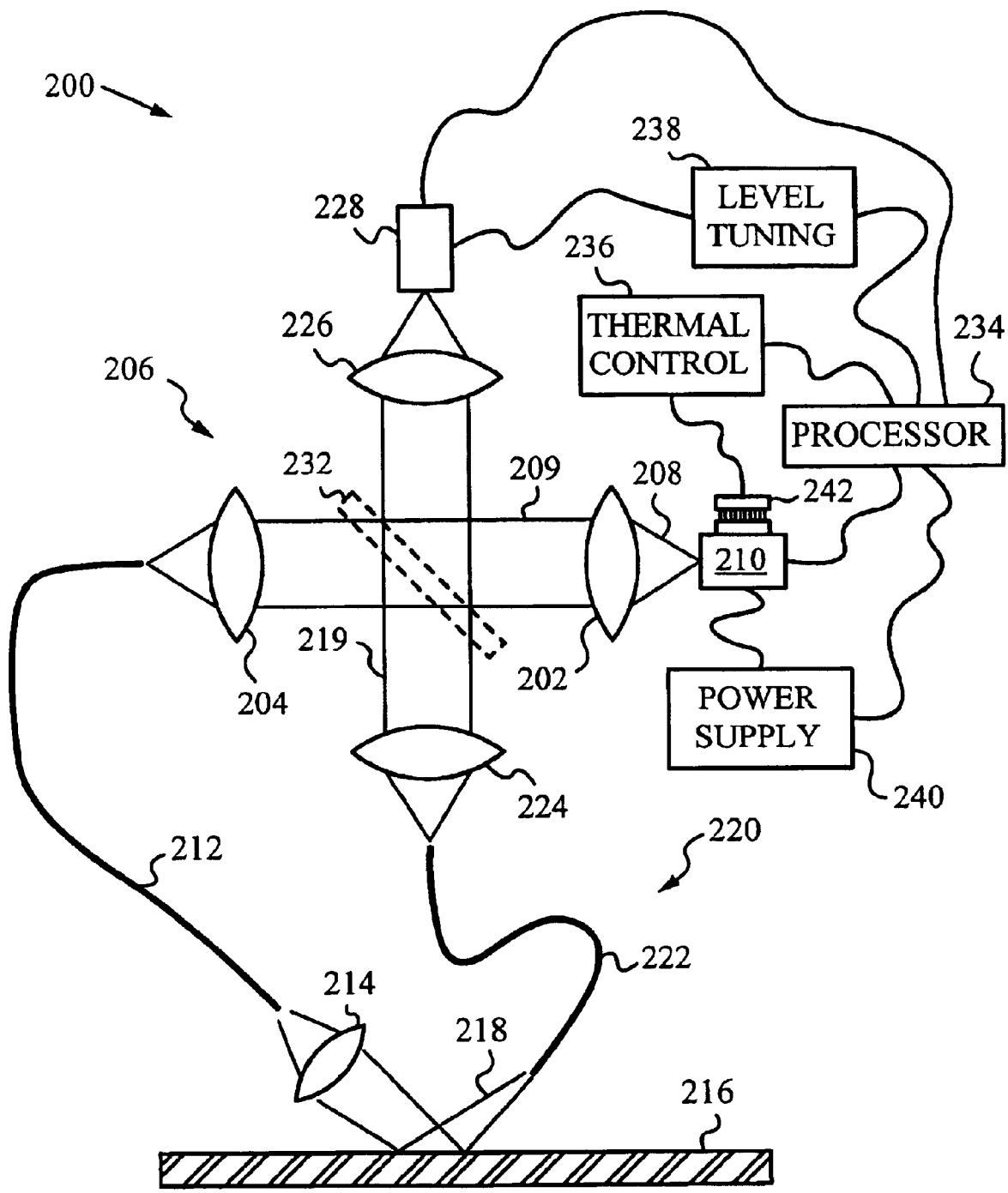
FIG. 5 is a schematic view of another embodiment of the optical system according to the invention using refractive optics.

FIG. 5 illustrates another embodiment of an optical system 200 according to the invention. System 200 uses refractive optics in the form of lenses 202, 204 in a first optical beam path 206. Lens 202 collimates a probe beam 208 emerging from a light source 210 to produce a collimated probe beam 209. Lens 204 focuses collimated probe beam 209 into an optical fiber 212. Fiber 212 delivers probe beam 208 to a focusing lens 214, which guides probe beam 208 to a calibration sample 216.

A response beam 218 in the form of reflected beam propagates from calibration sample 216 along a second optical beam path 220 and is in-coupled into an optical fiber 222. In fact, focusing lens 214 focuses probe beam 208 such that response beam 218 is in-coupled into fiber 222. Fiber 222 delivers response beam 218 to a second set of refractive optics in the form of lenses 224 and 226. These lenses collimate response beam 218 to a collimated response beam 219 and focus it on a detector 228 respectively.

As in the embodiment of FIGS. 3 and 4, optical system 200 has a beam crossing 230 between collimated probe and response beams 209 and 219. A reference sample 232 is placed at beam crossing when calibration is required.

Optical system 200 has a control unit consisting of several independent devices. In particular, a processor 234 connected to thermal control 236, a level tuner 238 and a power supply 240 constitute the control unit in this embodiment. During calibration processor 234 can adjust the sensitivity of detector 228 or its detector signal $I_d$ with the aid of level tuner 238. Alternatively, or in conjunction, processor 234 can adjust the source intensity $I_s$ by changing the drive current of light source 210 via power supply 240. If required, processor 234 can change the operating temperature of light source 210 with the aid of thermal control 236 to further tune source intensity $I_s$. More particularly, thermal control 236 is connected to a Peltier device 242 which cools or heats light source 242 depending on the signal from thermal control 236.

Optical system 200 of FIG. 5 can be used when $\Delta\lambda$ is not very large. Also, it can be used when very precise control of detector 228 and light source 240 is required.

Figure 6A:
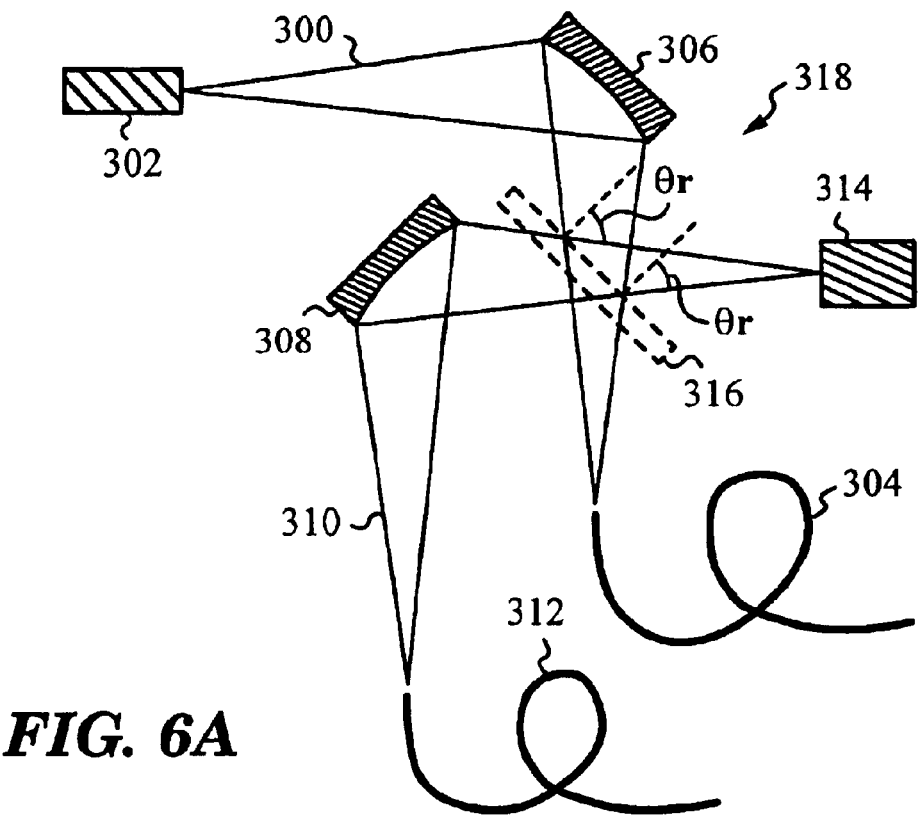
FIG. 6A illustrates a portion of another optical system according to the invention.

Another embodiment of the invention is shown in the partial view of FIG. 6A. In this case a probe beam 300 emitted from a light source 302 is focussed into a first fiber 304 by a first toroidal mirror 306. Also, a second toroidal mirror 308 is used to focus a response beam 310 returning from the calibration sample (not shown) via a second fiber 312 on a detector 314. A reference sample 316 is placed at a beam crossing 318 between probe and response beams 300, 310. As indicated above, non-collimated beams 300, 310 have different $\theta_r$.

Figure 6B:
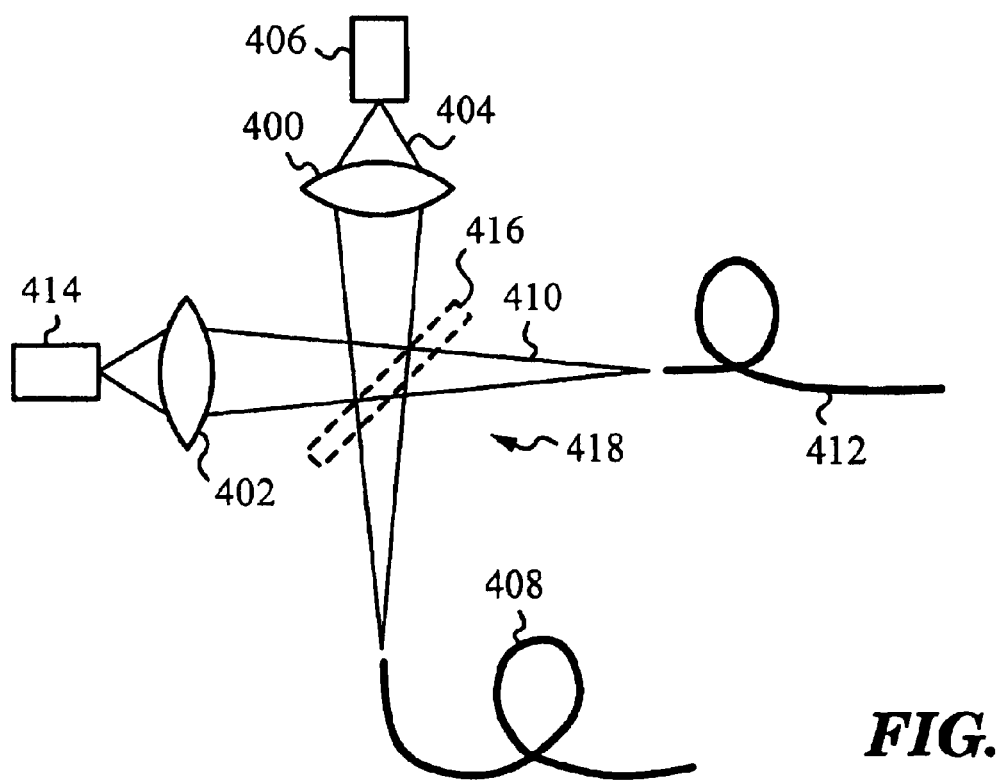
FIG. 6B illustrates a portion of still another optical system according to the invention.

Yet another alternative embodiment using refractive optics in the form of lenses 400 and 402 is shown in FIG. 6B. A probe beam 404 emitted from a light source 406 is focussed by lens 400 into a first fiber 408. First fiber 408 delivers probe beam 404 to a calibration sample (not shown). A response beam 410 returning from the calibration sample via second fiber 412 is focused by lens 402 on detector 414. A reference sample 416 is positioned at a beam crossing 418.

Optical systems in FIGS. 6A and 6B have fewer elements, thus lower cost of manufacturing.

It will be clear to one skilled in the art that the above embodiments may be altered in many ways without departing from the scope of the invention. Accordingly, the following claims and their legal equivalents should determine the scope of the invention.

What is claimed is:

1. A method for simultaneously compensating a source drift of a light source and a detector drift of a light detector, said method comprising:
   a) providing a first beam path with a crossing for a probe beam traveling from said light source to said light detector along a test location;
   b) providing a second beam path from said light source to said light detector along said crossing and not along said test location;
   c) positioning at said test location a calibration sample for sending a known response beam along said first beam path to said light detector in response to said probe bean;
   d) calibrating said light source and said light detector using said known response beam;
   e) temporarily placing a reference sample at said beam crossing for sending a reference beam along said second beam path to said light detector in response to said probe
   f) establishing a relation between said known response beam and said reference beam;
   g) defining a group of operational calibration parameters including a set time period, drift of said light source or drift of said light detector;
   h) positioning at said test location a test sample and testing said test sample;
   i) interrupting said testing in conjunction with said operational calibration parameters and temporarily placing said reference sample at said beam crossing for simultaneously compensating said source drift and said detector drift using said established relation while said test sample remains in position.

2. The method of claim 1, wherein said step of simultaneously compensating comprises establishing a relation between said known response beam and said reference beam.

3. The method of claim 1, further comprising placing a test sample at said test location such that said test sample sends a response beam along said second beam path to said light detector in response to said probe beam.

4. The method of claim 3, wherein said step of placing said reference sample at said beam crossing and said step of simultaneously compensating are performed while said test sample is at said test location.

5. The method of claim 1, wherein said calibration sample is a reflective calibration sample having a well-known reflectivity.

6. The method of claim 1, wherein said reference sample is selected such that the intensity of said reference beam is within a predetermined range of the intensity of said response beam.

7. The method of claim 1, further comprising the step of collimating said probe beam and said response beam at said beam crossing.

8. A system for simultaneously compensating a source drift of a light source and a detector drift of a light detector, said system comprising:
   a) a test location;
   b) a first beam path from said light source to said light detector along said test location;
   c) a beam crossing along said first beam path;
   d) a second beam path from said light source to said light detector along said beam crossing and not along said test location, said second beam path being substantially part of said first beam path;
   e) a calibration sample for positioning at said test location and for sending a known response beam along said second beam path to said light detector in response to said probe beam;
   f) a first control unit for calibrating said light source and said light detector using said known response beam;
   g) a reference sample for placing at said beam crossing for sending a reference beam along said second beam path to said light detector in response to said probe beam, wherein said reference sample is configured for being placed in response to at least one of a group of operational calibration parameters including a set time period, drift of said light source or drift of said light detector; and
   h) a second control unit for simultaneously compensating said source drift and said detector drift using a established relation between said known response beam and said reference beam.

9. The system of claim 8, further comprising a test sample for positioning at said test location for sending a response beam along said second beam path to said light detector in response to said probe beam.

10. The system of claim 9, wherein said reference sample is selected such that the intensity of said reference beam is within a predetermined range of the intensity of said response beam.

11. The system of claim 8, wherein said calibration sample is a silicon sample.

12. The system of claim 8, wherein said light source is selected from the group of light sources consisting of incandescent bulbs, lasers, and gas discharge tubes.

13. The system of claim 8, wherein said light source is a broadband light source.

14. The system of claim 8, wherein said light detector is selected from the group of light detectors consisting of broadband light detectors and photospectrometers.

15. The system of claim 8, wherein said calibration sample is reflective calibration sample having a well-known reflectivity.

16. The system of claim 8, further comprising a first toroidal mirror positioned in said first beam path.

17. The system of claim 16, further comprising a second toroidal mirror, said first toroidal mirror being positioned to collimate said probe beam to produce a collimated probe beam, said second toroidal mirror being positioned to focus said collimated probe beam.

18. The system of claim 8, further comprising a third toroidal mirror positioned in said second beam path.

19. The system of claim 18, further comprising a fourth toroidal mirror, said third toroidal mirror being positioned to collimate said response beam to produce a collimated response beam, said fourth toroidal mirror being positioned to focus said collimated response beam.

20. The system of claim 19, further comprising a first toroidal mirror positioned to collimate said probe beam to produce a collimated probe beam, and a second toroidal mirror being positioned to focus said collimated probe beam, said collimated probe beam crossing said collimated response beam at said beam crossing.

21. The system of claim 20, wherein a first optical length from said first toroidal mirror to said second toroidal mirror equals a second optical length from said first toroidal mirror to said fourth toroidal mirror passing through said beam crossing.

22. The system of claim 8, further comprising at least one lensing element positioned in said first beam path.

23. The system of claim 8, further comprising at least one lensing element positioned in said second beam path.

24. The system of claim 8, further comprising at least one optical fiber in said first beam path.

25. The system of claim 8, further comprising at least one optical fiber in said second beam path.

* * * * *